(12) United States Patent
Tsuchiya

(10) Patent No.: US 6,395,500 B1
(45) Date of Patent: May 28, 2002

(54) ANTIBODIES FOR THE DETECTION OF BEER SPOILAGE LACTIC ACID BACTERIA AND KIT EMPLOYING THE ANTIBODIES

(75) Inventor: Youichi Tsuchiya, Yaizu (JP)

(73) Assignee: Sapporo Breweries Limited, Tokyo (JP)

( * ) Notice: Subject to any disclaimer, the term of this patent is extended or adjusted under 35 U.S.C. 154(b) by 0 days.

(21) Appl. No.: 09/358,258

(22) Filed: Jul. 20, 1999

(30) Foreign Application Priority Data

Jul. 22, 1998 (JP) .......................................... 10-206484
Jan. 11, 1999 (JP) .......................................... 11-004096

(51) Int. Cl.$^7$ ..................... G01N 33/554; G01N 33/53; G01N 33/531; C07K 16/00; C12P 21/08
(52) U.S. Cl. ..................... 435/7.32; 435/961; 435/970; 435/7.1; 435/7.2; 435/7.9; 435/975; 530/388.2; 530/387.1; 530/388.1; 530/388.4; 436/808; 436/810; 436/530
(58) Field of Search ........................... 530/388.2, 387.1, 530/388.1, 388.4; 435/7.32, 7.1, 7.2, 975, 7.9, 961, 970; 436/808, 810, 530

(56) References Cited

U.S. PATENT DOCUMENTS 4,833,074 A * 5/1989 Fagerhol et al. ................ 435/7

OTHER PUBLICATIONS

Yasui et al. J. Fermentation & Bioengineering 84: 35–40, Sep., 1997.*
Yasui et al. FEMS Microbiol. Lett. 151(2): 169–176, Jun. 15, 1997.*
Dolezil et al. J. Inst. Brew. 81: 281–286, 1975.*
Laurent et al. Proc. Congr. Eur. Brew. Conv. 24th, pp. 487–492, 1993.*
Tanabe et al. Bull. Fac. Agricult. 33: 53–63, 1983.*
Hutter et al. Brauwelt 131: 1797–1802, 1991.*
Hutter et al. Brauwelt 131: 726–730, 1991.*
Rinck et al. Brauwissenchaft 40: 324–327, 1987.*
Yasui et al. Appl. Environ. Microbiol. 63: 4528–4533, Nov., 1997.*
Whiting et al. Appl. Environ. Microbiol. 40: 713–716, 1997.*
Derwent Abstracts, Asahi Breweries, "Monoclonal Antibody Against Lactic Acid Bacterium and Method For Detecting Lactic Acid Bacterium With the Same," JP 6046881 A, Feb. 22, 1994.
Derwent Abstracts, Asahi Breweries, "Monoclonal Antibody Specific to Lactobacillus and Detection of Lactobacillus Using the Antibody," JP 6311895 A, Nov. 8, 1994.
Derwent Abstracts, AN 97372530, "Purification and Partial Characterization of an Antigen Specific to Lactobacillus Brevis Strains With Beer Spoilage Activity," Oct. 2, 1997 and T. Yasui, et al., Fems Microbiology Letters, vol. 151, No. 2, pp. 169–176, Jun. 15, 1997.
Derwent Abstracts, Sapporo Breweries, "Detection of Bacteria Harmful for Beer Brewering," JP 570591664, Apr. 9, 1982.

* cited by examiner

Primary Examiner—S. Devi
(74) Attorney, Agent, or Firm—Oblon, Spivak, McClelland, Maier & Neustadt, P.C.

(57) ABSTRACT

Antibodies capable of detecting a beer spoilage lactic acid bacterium. Lactic acid bacteria possessing beer spoilage ability are grown in beer, a mammal is immunized to produce antibodies for the detection of beer spoilage lactic acid bacteria, and the beer spoilage lactic acid bacteria are detected using the antibodies. Further, by employing the antibodies, there are provided a method and a kit for detecting a beer spoilage lactic acid bacterium specifically, rapidly, conveniently, and reproducibly, which bacterium contaminates the process of beer production, grows in the produced beer, and lowers the quality of the beer.

5 Claims, 1 Drawing Sheet

(1 of 1 Drawing Sheet(s) Filed in Color)

Fig. 1

| Antibody Solution | | | |
|---|---|---|---|
| I | II | III | |
| ● | ● | ● | *Non-beer spoilage lactic acid bacterium* |
| ● | ● | ● | *Beer spoilage L. brevis* |
| ● | ● | ● | *Beer spoilage L. lindneri* |
| ● | ● | ● | *Beer spoilage*    *Pediococcus* 8022 strain |
| ● | ● | ● | *Beer spoilage*    *Pediococcus* 8023 strain |

ANTIBODIES FOR THE DETECTION OF BEER SPOILAGE LACTIC ACID BACTERIA AND KIT EMPLOYING THE ANTIBODIES

BACKGROUND OF THE INVENTION

1. Field of the Invention

The present invention relates to antibodies that recognize beer spoilage lactic acid bacteria capable of growing in beer, a method for detecting the beer spoilage lactic acid bacteria using the antibodies, and a kit for identification of the beer spoilage lactic acid bacteria.

2. Background of the Invention

There is a recognized danger that once a certain kind of lactic acid bacterium has contaminated the process of beer production, haze, off-flavors or the like, caused by the bacterium, may impair the quality of the produced beer. For example, representative beer spoilage bacteria include certain species of lactic acid bacterium belonging to the Lactobacillus genus, especially those belonging to *Lactobacillus brevis* and *Lactobacillus lindneri*, as well as include certain species of lactic acid bacterium belonging to the Pediococcus genus. Thus, attempts have been made to develop methods for the rapid and high sensitivity detection of these beer spoilage lactic acid bacteria.

Specifically mentioned is a method in which after the beer to be analyzed is filtrated with a membrane filter, it is grown in a suitable medium and the grown colonies are observed. However, since beer spoilage bacteria existing in beer are presented in minute quantities and their growth in the medium is slow, there are problems with the sensitivity and the time-consuming nature of their detection using this method.

A method for the detection of beer spoilage lactic acid bacteria in beer that utilizes antigen-antibody reaction has been developed. For example, polyclonal antibodies (antisera) against lactic acid bacteria have been prepared. (Sharpe, M. E., J. Gen. Microbiol., 12, 107 (1955); Sharpe, M. E., Int. J. Syst. Bacteriol., 20, 509 (1970); Knox, M. W. et al., Infect. Immun., 24, 12 (1979); Shimohashi, H. and Mutai, M., J. Gen. Microbiol., 103, 337 (1977); and Japanese Unexamined Patent Appln. Publn. Hei 4-72570.) At present, by adjusting various conditions, it has become possible to prepare antisera of such quality that both their specificity and their sensitivity are, to a certain degree, acceptable for practical use. Further improvements however remain to be desired in the following aspects, among others: the antibody titer or the specificity of an antiserum unavoidably fluctuates with its lot; antiserum against a certain kind of lactic acid bacterium turns positive against non-beer spoilage bacteria as well; and some antisera require NaOH treatment.

For these reasons, detection methods employing monoclonal antibodies have been proposed. (Japanese Unexamined Patent Appln. Publn. Hei 6-46881 and Japanese Unexamined Patent Appln. Publn. Hei 6-105698). According to the description of Japanese Unexamined Patent Appln. Publn. Hei 6-46881, monoclonal antibodies are prepared using as antigens, *Lactobacillus brevis, Lactobacillus collinoides* and *Lactobacillus suebicus* that belong to Group 3 of the Lactobacillus genus and that are grown in media; and these monoclonal antibodies are used to detect Group 3 of the Lactobacillus genus in beer.

However, the lactic acid bacteria, which will prove to grow in beer production, are only part of those belonging to Group 3 of the Lactobacillus genus. Therefore, the method as described in Japanese Unexamined Patent Appln. Publn. Hei 6-46881 has a problem that other non-beer spoilage lactic acid bacteria may also be detected, i.e., false positive results are obtained with this method.

According to the description of Japanese Unexamined Patent Appln. Publn. Hei 6-105698, a monoclonal antibody is prepared using as an antigen, *Lactobacillus plantarum* that belongs to the Lactobacillus genus and that is grown in medium; and this monoclonal antibody is used to detect the Lactobacillus and *Lactobacillus coryniformis* in beer. However, this disclosed antibody has the same problem that it also detects non-beer spoilage lactic acid bacteria (false positives).

Consequently, there has been proposed a method to detect only beer spoilage bacteria that can grow in beer (hereinafter referred to as "beer spoilage ability"). (Japanese Unexamined Patent Appln. Publn. Hei 10-104238.) According to the method as described in Japanese Unexamined Patent Appln. Publn. Hei 10-104238, an antiserum is prepared with rabbits using as an antigen, *Lactobacillus brevis* that possesses no glucose assimilation ability under anaerobic conditions and that is grown in medium; and the antiserum is used to detect the *Lactobacillus brevis* that possesses the beer spoilage ability. The thus prepared antiserum is believed to specifically react with *Lactobacillus brevis* and *Pediococcus damnosus*, both of which cause the beer spoilage ability.

Nevertheless, to remove from the antiserum nonspecific antibodies that react with *Lactobacillus brevis* (i.e., nonspecific antibodies that react with non-beer spoilage lactic acid bacteria), the alkali-treated cells of non-beer spoilage *Lactobacillus brevis* must be used to effect removal of the nonspecific antibodies by adsorption, according to the method as described in Japanese Unexamined Patent Appln. Publn. Hei 10-104238. In addition, a problem exists in that depending on the *Lactobacillus brevis* to be used as the antigen, the resulting antiserum is prone to false recognition. Further, now that antiserum is used, its antibody titer and specificity unavoidably fluctuates from lot to lot.

As a representative beer spoilage lactic acid bacterium mentioned is *Lactobacillus lindneri*; but the effectiveness of the antiserum against such bacterium is not noted in the publication of Japanese Unexamined Patent Appln. Hei 10-104238.

In view of the foregoing, improved methods of detecting bacteria which are spoilage to beer are needed in the fermentation industry.

SUMMARY OF THE INVENTION

It is an object of the present invention to provide reagents capable of detecting a lactic acid bacterium which is beer spoilage to the quality of beer.

It is another object of the present invention to provide a method for the specific, rapid, convenient, and reproducible detection of a beer spoilage lactic acid bacterium which contaminates into the process of beer production and grows in the produced beer and that degrades the quality of the beer.

It is another object of the present invention to provide a method for the efficient and exhaustive detection of a beer spoilage lactic acid bacterium such as *Lactobacillus brevis, Lactobacillus lindneri*, or *Pediococcus damnosus*.

An additional object of the present invention is to provide an identification kit for accurately and conveniently predicting the beer spoilage ability of a lactic acid bacterium that has emerged from conventional culturing with medium.

The objects of the invention, and others, may be accomplished with an antibody for the detection of a beer spoilage lactic acid bacterium that is produced by growing a lactic acid bacterium with the beer spoilage ability in beer and by immunizing a mammal with the beer.

The objects of the invention may also be accomplished with a monoclonal antibody that displays reactivity against a lactic acid bacterium showing spoilage to beer and that displays no reactivity against a non-beer spoilage lactic acid bacterium, where the antibody is produced by growing a lactic acid bacterium with the beer spoilage ability in beer and by immunizing a mammal with the beer.

The objects of the invention may be accomplished the antibody for the detection of a beer spoilage lactic acid bacterium, as well as the monoclonal antibody as described above, where the lactic acid bacterium with beer spoilage ability is a lactic acid bacterium possessing the glucose assimilation ability under anaerobic conditions.

The objects of the invention may also be accomplished with the antibody for the detection of a beer spoilage lactic acid bacterium, as well as the monoclonal antibody as described above, where the lactic acid bacterium with the beer spoilage ability is a lactic acid bacterium selected from the group consisting of beer spoilage *Lactobacillus brevis*, beer spoilage *Lactobacillus lindneri*, and beer spoilage *Pediococcus damnosus*.

The objects of the invention may also be accomplished a method for the detection of a beer spoilage lactic acid bacterium with beer spoilage ability such as *Lactobacillus brevis, Lactobacillus lindneri*, and *Pediococcus damnosus* using the antibody described above.

The objects of the invention may be accomplished a hybridoma cell line, e.g., BLb2F37 (FERM BP-6744), BG3A5b4 (FERM BP-6745), or PQ3H8a9 (FERM BP-6746), that produces the monoclonal antibody specifically reacting with a beer spoilage lactic acid bacterium.

The objects of the invention may also be accomplished with a method for the detection of a beer spoilage lactic acid bacterium with the beer spoilage ability such as *Lactobacillus brevis, Lactobacillus lindneri*, and *Pediococcus damnosus*, using a combination of the monoclonal antibodies produced by the hybridomas.

The objects of the invention may also be accomplished with a kit for the identification of a beer spoilage lactic acid bacterium, having at least the following components: (1) a centrifugation tube equipped with a filter for trapping bacteria; (2) a monoclonal antibody produced by the hybridoma according to the invention; (3) a secondary antibody or an antibody-like substance against the aforementioned antibody each of which is labeled with enzyme; and (4) a substrate reacting with and coloring the labeling enzyme of the secondary antibody or of the antibody-like substance.

The objects of the invention may also be accomplished with methods of making the antibodies and hybridomas described above.

BRIEF DESCRIPTION OF THE DRAWING

The file of this patent contains at least one drawing executed in color. Copies of this patent with color drawing will be provided by the Patent and Trademark Office upon request and payment of the necessary fee.

A more complete appreciation of the invention and many of the attendant advantages thereof will be readily obtained as the same becomes better understood by reference to the following detailed description when considered in connection with the accompanying drawing, wherein:

FIG. 1 shows the results obtained in Example 3, i.e., the quick identification using three types of antibodies.

DETAILED DESCRIPTION OF THE INVENTION

The present invention has wide applicability. The antibodies of this invention display reactivity against beer spoilage lactic acid bacteria, but display no reactivity against non-beer spoilage lactic acid bacteria; therefore, they are useful for the rapid, convenient, and high accuracy detection of the beer spoilage lactic acid bacteria. In addition, because the antibodies of the invention are monoclonal antibodies and thus can be prepared reproducibly, they are useful as the reagents for the detection of beer spoilage bacteria. Further, by combining the antibodies of the invention, it is possible to detect lactic acid bacteria of all kinds that are regarded problematic. Moreover, the quick identification method and a kit therefor according to the invention employ a commercially available centrifugation tube equipped with a filter and take advantage of the specificity the three antibodies of the invention possess. This enables convenient and accurate judgements on the beer spoilage ability with respect to the lactic acid bacteria that have emerged from conventional culturing with media.

Beer Spoilage Lactic Acid Bacteria

As used herein, the term "a beer spoilage lactic acid bacterium (or bacteria)" refers to a bacterium that is capable of growing in beer and that causes haze in the beer due to its growth therein.

The terms reacting, reacting with, binding etc., used herein in reference to the interaction between the inventive antibody and the lactic acid bacterium, refer to the formation of a complex between the antibody and the bacterium, i.e., an antibody-antigen reaction. The formation of such complexes, or the lack thereof, is in reference to analytically relevant conditions used in beer production, such as in phosphate-buffered saline (PBS) at 25° C. (see the Examples below).

Representatives of the beer spoilage lactic acid bacteria include, for example, bacteria classified as *Lactobacillus brevis, Lactobacillus lindneri*, or *Pediococcus damnosus* (see Back, W. et al.; Brauwlt, 31/32, 1358 (1988), incorporated herein by reference); but not all these bacteria are spoilage to beer.

The lactic acid bacteria that are used as antigens in this invention are those possessing beer spoilage ability such as lactic acid bacteria belonging to *Lactobacillus brevis, Lactobacillus lindneri*, or to the *Pediococcus damnosus* genus.

These beer spoilage lactic acid bacteria can be obtained by adding a sample derived from the environment to beer, directly or after having grown lactic acid bacteria by the use of a selection medium of lactic acid bacterium and by selecting those which cause haze.

Subculturing and preservation of the beer spoilage lactic acid bacteria are carried out in the following manner: the bacteria are grown in beer, preserved at 4° C., and are subcultured every few months; or alternatively, glycerol is added so as to give a final concentration of 20%; and the bacteria are preserved at −70° C.

Determination of the spoilage to beer may be conducted in the following manner: about $10^7$ bacterial cells are added to a small bottle (334 ml) containing a commercially available beer—100% malt, pH of about 4.4, and a bitterness unit of about 28—; it is capped and stored at 25° C. for two months; and then, a visual inspection is made to judge whether or not haze was produced in the beer.

Monoclonal Antibodies

According to well-known methods, mice were immunized with the beer spoilage lactic acid bacteria that were selected as described above. Subsequently, hybridomas were prepared and the hybridoma clones producing desired monoclonal antibodies were established. Procedures for preparing monoclonal antibodies and hybridomas is described in *Current Protocols in Molecular Biology*, Vol. 1–3, Ausubel et al, Eds., John Wiley and Sons, 1998, incorporated herein by reference in its entirety.

1. Preparation of Antigen and Immunization

Specifically, the beer spoilage lactic acid bacterium that has been grown in beer is harvested. After washing with physiological saline, bacterial cells are suspended in phosphate buffered saline (PBS) and used to immunize mice. Additional immunizations are done several times at appropriate intervals and a final immunization is to be conducted when the antibody titer in blood rises.

2. Cell Fusion

Spleen of the immunized mouse is extracted three days after the final immunization. The spleen cells are fused to myeloma cells in the presence of a suitable cell fusion agent. The fused cells are inoculated onto a 96-well microplate and culturing is performed in a suitable selection medium, e.g., HAT medium.

3. Screening and Cloning

According to a method such as ELISA, a hybridoma that will produce the desired antibody is selected and screening is performed.

Cloning is performed on the hybridoma that produces the desired antibody using a method such as limiting dilution and a hybridoma clone is established.

4. Preparation of Monoclonal Antibody in a Large Quantity

After the hybridoma clone producing the antibody is grown in medium, the cells are recovered and then, inoculated intraperitoneally into a mouse stimulated with the pristane before use. An ascites containing the antibody is collected from its intraperitoneum. Subsequently, a monoclonal antibody is purified from the ascites using the ammonium sulfate precipitation or an affinity column, e.g., Protein A or Protein G column. Alternatively, after the hybridoma clone is grown in medium on a large scale, the monoclonal antibody is purified from the culture according to a method using the ammonium sulfate precipitation, an ion-exchange column or the like.

The monoclonal antibodies thus obtained have the properties of: displaying reactivity against lactic acid bacteria showing the beer spoilage ability; and displaying no reactivity against non-beer spoilage lactic acid bacteria.

5. Detection of Beer Spoilage Lactic Acid Bacteria

Exemplary methods for detection of the beer spoilage lactic acid bacteria include ELISA (Biosci. Biotech. Biochem., 5, 2039 (1995), incorporated herein by reference)), a method relying on the antigen-antibody reaction of bacteria trapped on membranes (Japanese Unexamined Patent Appln. Publn. Hei 6-46881, incorporated herein by reference), and the like.

Specifically, a produced beer is filtered with a membrane filter to trap the bacteria in the beer. Subsequently, after washing the membrane with a suitable buffer such as phosphate buffered saline (PBS), the bacteria are allowed to react with the monoclonal antibodies as obtained above and the membrane washed with PBS. Then, the monoclonal antibodies remaining on the membrane are detected using an anti-mouse antibody conjugated with peroxidase, which will enable the detection of beer spoilage lactic acid bacteria.

Further, if the antibodies obtained in this invention are directly labeled (e.g., with enzymes, fluorescent dyes or radioisotopes), the direct detection of the beer spoilage lactic acid bacteria becomes possible without requiring secondary antibodies; and the detection sensitivity can also be enhanced.

6. Quick Identification Method and Kit

The method according to this invention having high specificity and allowing quick identification is provided with at least the following components: viz. (1) a centrifugation tube equipped with a filter for trapping bacteria; (2) the three kinds of monoclonal antibody against beer spoilage lactic acid bacteria as obtained according to the invention; (3) secondary antibodies or antibody-like substances against the aforementioned monoclonal antibodies, both of which are labeled with enzymes,; and (4) a substrate reacting with and coloring the labeling enzymes of the secondary antibodies or of the antibody-like substances. Furthermore, the lactic acid bacteria that are used as positive controls may preferably be contained.

The quick identification method, the method of detection and the quick identification kit according to the invention, will be explained in detail hereinbelow.

The quick identification kit for beer spoilage lactic acid bacteria according to the invention relies on trapping of bacteria by the use of a centrifugation tube equipped with a filter and the removal of unreacted antibodies, in combination with enzyme immunoassay; it judges the prediction of the beer spoilage ability concerning a test bacterium by the magnitude of its color tone. In the present method, a bacterial suspension and enzyme-labeled antibodies (e.g., monoclonal antibodies and enzyme-labeled secondary antibodies, or monoclonal antibodies directly labeled with enzymes) are added to the centrifugation tube with a filter and subjected to centrifugation. When the antibody reacts with the test bacterium, it remains on the filter together with the labeling enzyme; whereas, when the antibody does not react, the labeling enzyme is removed together with the filtrate under the filter. Thus, when an enzyme substrate solution is added, coloring occurs only where the antibody reacts with the test bacterium. This enables the prediction of the beer spoilage ability of the test bacterium to be made with ease. In addition, the specificity is high because the fundamental principle is the same as that of the direct fluorescent antibody technique.

It is required that the filter for use in the centrifugation tube with a filter have a pore diameter which is large sufficient to trap the lactic acid bacteria to be the object of measurement and which allows the removal of unreacted antibodies. This can be readily chosen by one skilled in the art. For example, a filter having a pore diameter on the order of 0.2–0.45 $\mu$m and of such material that minimizes the adsorption of protein, e.g., polyvinylidenefluoride (PVDF), may be employed; preferably, it is used after blocking with casein, bovine serum albumin or the like.

The test bacterium is suspended in physiological saline or a buffer suitable for the antigen-antibody reaction; and then, the monoclonal antibodies and the enzyme-labeled secondary antibodies or the monoclonal antibodies directly labeled with enzymes are added.

After allowing them to react with the test bacterium, the unreacted monoclonal and enzyme-labeled secondary antibodies or the unreacted monoclonal antibodies directly labeled with enzymes are removed by centrifugation.

Furthermore, to the antibodies is added a washing solution of such nature and concentration that does not inhibit the reaction, e.g., 10 MM Tris-HCl (pH 8.0) containing 0.05% TWEEN 20 (polyoxyethylene(20) sorbitan monolaurate). Thereafter, washing and removal of the washing solution are carried out by centrifugation. According to this invention, by employing the centrifugation tube with a filter (or a filter unit), it is possible to carry out washing and removal of washing solution simultaneously and it also becomes possible to completely carry out the washing with great efficiency without the risk of the test bacteria being washed away.

It is preferred that the coloring substrate have its absorption maximum wavelength in a visible region, be highly sensitive and readily distinguishable, and possess high stability over time. To meet such requirements, coloring substrates of the peroxidase type are preferable. For example, tetramethylbendizine (TMBZ) and orthophenylenediamine (OPD) may be used.

The kit according to this invention is to be used to identify the beer spoilage lactic acid bacteria. A specific example of a series of manipulations according to this embodiment is illustrated in what follows:

1. A physiological saline, 100 μl, and a beer spoilage lactic acid bacterial suspension—suspended in physiological saline, sterilized by heat treatment and its absorbance at 660 nm adjusted to 0.3—, 100μl which is used as a positive control, are respectively placed on an agglutination dish.
2. One platinum loop of the test bacterium is suspended in the physiological saline: its concentration is adjusted to be nearly the same level as that of the beer spoilage lactic acid bacterial suspension.
3. Each 25 μl of the respective bacterial suspensions is added to three filter units: three filter units are used for one bacterium and designated numbers I–III.
4. An antibody solution, 50 μl, is added to the respective filter units: the antibody solution is obtained by diluting with PBS, a monoclonal antibody and an enzyme-labeled secondary antibody, a monoclonal antibody directly labeled with enzyme, or the like to give an appropriate concentration; and to I is added a solution of BLb2F37 for use as the monoclonal antibody, to II added a solution of BG3A5b4 for use, and to III added a solution of PQ3H8a9 for use.
5. After agitation, the filter units are allowed to stand at room temperature for 15 min.
6. The units are centrifuged at 2000 rpm for 5 min.
7. To the units is added 350 μl of a washing solution.
8. The units are centrifuged at 2000 rpm for 10 min.
9. To the units is added 50 μl of a substrate solution.
10. After agitation, the filter units are allowed to stand at room temperature for 5 min.
11. To the units is added 50 μl of a quenching solution.
12. After agitation, it is first to be ascertained that the filter units to which the positive control has been added show adequate coloring.
13. Next, the mode of coloring with respect to the three filter units, to which the test bacterium has been added, is compared to the following table and a judgement is to be made.

Judgement Table
("+": strong coloring, "–": no coloring or weak coloring)

| antibody solution | | | |
|---|---|---|---|
| I | II | III | judgement result |
| – | – | – | non-beer spoilage bacterium |
| + | – | – | beer spoilage *L. brevis* or *P. damnosus* |

-continued

Judgement Table
("+": strong coloring, "–": no coloring or weak coloring)

| antibody solution | | | |
|---|---|---|---|
| I | II | III | judgement result |
| – | + | – | beer spoilage *L. lindneri* |
| – | – | + | beer spoilage *P. damnosus* |
| + | – | + | beer spoilage *L. brevis* or *P. damnosus* |

When any beer spoilage lactic acid bacterium is allowed to react respectively with the three monoclonal antibodies, it does react with either one or two monoclonal antibodies and, at the same time, does not react with at least one monoclonal antibody. On the other hand, a non-beer spoilage bacterium does not react with any of the three monoclonal antibodies. The present judgement method utilizes the foregoing: see the section of Assays for Antibody Specificity in the Examples. In other words, unless the concentration of the initially provided bacterial suspension is too low or too high, any beer spoilage bacterium develops markedly strong color in at least one or two of the filter units as compared to the remaining unit(s) when the suspension is allowed to react with equivalent amounts of the three antibodies; whereas, in cases of non-beer spoilage bacteria none of the three develops color, or weak coloring of similar magnitude occurs in all the three. Accordingly, the quantity of a test bacterium need not be precise in this method; and moreover, when the bacterium has been judged to have the beer spoilage ability, identification of the kind of bacterium is also possible based on which filter unit has developed color. In addition, since the suspension of beer spoilage lactic acid bacterium is processed simultaneously and used in a comparison as the positive control, it is possible to determine whether the antibodies have been inactivated, as well as to determine whether the manipulation procedure is in error. At the same time, more accurate judgements are enabled.

It occasionally happens that certain beer spoilage bacteria experience diminished reactivity against antibodies when their subculturing is repeated in medium too many times after having been isolated from beer. In such cases, the bacteria are, for example, first suspended in about 0.1% NaOH solution and allowed to stand at room temperature for 10 min. Then, they are added to the filter units. After the NaOH solution was removed by centrifugation, the antibody solutions are to be added. Thus, adequate coloring can be attained.

Having generally described this invention, a further understanding can be obtained by reference to certain specific examples which are provided herein for purposes of illustration only and are not intended to be limiting unless otherwise specified.

EXAMPLES

Example 1

Preparation of Monoclonal Antibodies Specific for the Beer Spoilage Lactic Acid Bacteria
(1) Preparation of Antigens

*Lactobacillus brevis, Lactobacillus lindneri* and *Pediococcus damnosus*, which were the beer spoilage lactic acid bacteria isolated from beer, were used as antigens. These strains were identified according to the classification system as described in Bergey's Manual of Systematic Bacteriology, incorporated herein by reference. Notably, as stated in the classification system, the *Lactobacillus brevis* used possesses the glucose assimilation ability under anaerobic conditions. These strains that had been preserved in beer at 4° C. were inoculated in fresh beers and grown at 25° C. until the beers turned turbid, and cells harvested by centrifugation. Then, portions of the bacterial solutions were subcultured in fresh beers, and fresh bacterial cells were used at each time of immunization.

After the cells harvested by centrifugation were washed with physiological saline, they were suspended in phosphate buffered saline (PBS) and adjusted their absorbance at 660 nm to 0.5 for immunization.

(2) Immunization of Mice

Female BALB/C mice (8 weeks of age) were purchased from Japan SLC. After feeding preliminarily for 10 days, they were immunized.

As for immunization, three kinds of bacterial suspension as prepared above were inoculated intraperitoneally into respective mice. The interval of injection was scheduled to be once a week, and the amounts of injected suspension were, from the time of start, 0.1, 0.5, 1.0, 1.0, 1.0, and 1.0—6 times in total: a total of 4.6 ml was injected.

(3) Cell Fusion

Three days after the final immunization, spleens were removed from the mice and the spleen cells were separated in a RPMI1640 medium without fetal bovine serum (FCS)—Nissui Pharmaceutical Co. Ltd.—according to Monoclonal Antibody Experimental Manual; Toyama, S; Yasuto, T., Ed.; Kodansha. Next, the cells were subjected to cell fusion with myeloma cells (SP2/0·Ag14, Dainippon Pharmaceutical Co. Ltd.) in the presence of polyethylene glycol (for use in cell fusion, available from Behringer Manheim AG.). Subsequently, the hybridoma was suspended in a RPMI1640 medium containing 15% FCS and HAT (H-0262, available from Sigma Inc.). The suspension was plated in a 96-well microplate (No. 167008 available from Nunc Inc.), grown at 37° C. in a $CO_2$ incubator, and thereafter, the medium was exchanged at appropriate intervals. When the hybridoma was grown, the antibody titer of the supernatant was measured by ELISA as described below and antibody-positive cells were screened for.

(4) Screening for Antibodies

To each well of a 96-well microplate (No. 168055 available from Nunc Inc.) was added each 50 μl of a 2.5% glutaraldehyde solution. After allowing to stand at room temperature for 3 h, the solution was discarded. Preparations of beer spoilage lactic acid bacteria of the three kinds, which had been subcultured in beer, and a preparation of *Lactobacillus casei* AHU1057 strain (control), which was a non-beer spoilage lactic acid bacterium that had been subcultured in an MRS medium, were made respectively so that their absorbance at 660 nm could be 0.3: AHU: Laboratory of Culture Collection of Microorganisms, Faculty of Agriculture, Hokkaido University, Sapporo, Japan. The respective preparations were added to each well in 50 μl portions. After centrifugation at 2,000 rpm for 5 min, the wells were allowed to stand at 4° C. till the next day. Then, the supernatant was discarded, and 100 μl of PBS containing 1% gelatin was added to the each well. After allowing to stand at room temperature for 2 h, the supernatant was discarded and an assay plate on which the bacteria had been coated was prepared.

The culture supernatant from the cell fusion, 50 μl, was added to each well of the assay plate as prepared above. Further, to the each well was added 25 μl of a commercially available peroxidase-conjugated anti-mouse IgG+M antibody (Wako Pure Chemicals), diluted 250-folds with PBS containing 0.1% gelatin. After allowing to stand at room temperature for 1 h, the supernatant was discarded. Then, the each well was twice washed with 100 μl of a Tris buffer (10 mM Tris-HCl, pH 8.0) containing 0.05% TWEEN 20 (polyoxyethylene(20) sorbitan monolaurate). Subsequently, 50 μl of a substrate solution (0.25 M sodium citrate buffer (pH 4.2) containing 1 mg/ml o-phenylenediamine dihydrochlorides) was added to the each well. After allowing to stand at room temperature for 5 min, 50 μl of a quenching solution (10 mM $NaN_3$) was added to the each well to terminate the reaction. "A492–A630" (values obtained by subtraction of the absorbance at 630 nm from that at 492 nm) was measured. If the well coated with a beer spoilage lactic acid bacterium had higher absorbance than does the well coated with *Lactobacillus casei* (the control), it was determined to be positive.

(5) Cloning

Cloning was performed on the hybridomas having displayed positiveness, according to limiting dilution. In this way, four monoclonal antibody-producing hybridomas were obtained from the hybridomas which utilized *Lactobacillus brevis* as the antigen. Among them, one strain was designated "BLb2F37" and deposited with National Institute of Bioscience and Human-Technology, Agency of Industrial Science and Technology, Ministry of International Trade and Industry on Jul. 8, 1998 (Accession No. FERM P-16884). The strain was further made "international deposit" with National Institute of Bioscience and Human-Technology, Agency of Industrial Science and Technology, Ministry of International Trade and Industry (1-3, Higashi 1 chome, Tsukuba-shi, Ibaraki-ken 305-8566, JAPAN), an international depository authority, on Jun. 4, 1999 (International Accession No. FERM BP-6744). Also, two monoclonal antibody-producing hybridomas were obtained from the hybridomas which utilized *Lactobacillus lindneri* as the antigen. Between them, one strain was designated "BG3A5b4" and deposited with National Institute of Bioscience and Human-Technology, Agency of Industrial Science and Technology, Ministry of International Trade and Industry on Jul. 8, 1998 (Accession No. FERM P-16885). The strain was further made "international deposit" with National Institute of Bioscience and Human-Technology, Agency of Industrial Science and Technology, Ministry of International Trade and Industry (1-3, Higashi 1 chome, Tsukuba-shi, Ibaraki-ken 305-8566, JAPAN), an international depository authority, on Jun. 4, 1999 (International Accession No. FERM BP-6745). In addition, two monoclonal antibody-producing hybridomas were obtained from the hybridomas which utilized *Pediococcus damnosus* as the antigen. Between them, one strain was designated "PQ3H8a9" and deposited with National Institute of Bioscience and Human-Technology, Agency of Industrial Science and Technology, Ministry of International Trade and Industry on Jul. 8, 1998 (Accession No. FERM P-16886). The strain was further made "international deposit" with National Institute of Bioscience and Human-Technology, Agency of Industrial Science and Technology, Ministry of International Trade and Industry (1-3, Higashi 1 chome, Tsukuba-shi, Ibaraki-ken 305-8566, JAPAN), an international depository authority, on Jun. 4, 1999 (International Accession No. FERM BP-6746).

(6) Preparation of Monoclonal Antibodies

The hybridomas had been grown until ca. 80% of the total cells dwarfed and looked blackish, and then, cells were removed by centrifugation. To these was slowly added saturated ammonium sulfate in amounts equivalent to the culture supernatants at 4° C. After centrifugation, the supernatants were discarded. After the precipitates were dissolved in PBS again, the dissolved solutions were dialyzed in PBS at 4° C. overnight to prepare monoclonal antibodies.

(7) Assays for Antibody Specificity

The specificity of the monoclonal antibodies obtained above (BLb2F37, BG3A5b4 and PQ3H8a9 antibodies) was investigated against the following strains isolated at the beer breweries and research laboratories: 44 strains displaying spoilage to beer and 18 strains displaying non-spoilage to beer, both of which belong to *Lactobacillus brevis*; seven strains displaying spoilage to beer and belonging to *Lactobacillus lindneri*; three strains displaying spoilage to beer and one strain displaying non-spoilage to beer, both of which belong to *Pediococcus damnosus*; and 47 strains of other lactic acid bacteria displaying non-spoilage to beer, including *Lactobacillus casei, Lactobacillus parvus, Lactobacillus plantarum, Lactobacillus fructivorans, Lactobacillus coryniformis, Lactobacillus acidophilus, Lactobacillus buchneri, Lactobacillus collinoides, Lactobacillus hilgardii, Lactobacillus kandleri, Lactobacillus kefir, Pediococcus pentosaceus,* and *Pediococcus dextrinicus*.

The respective strains were grown and cells were harvested; they were used to assay the reactivity against each strain similarly to the method as described in (4). Here, the beer spoilage strains were grown in beer and the non-beer spoilage strains were grown in MRS medium. As the control, the strain of *Lactobacillus casei* AHU1057, which did not display spoilage to beer, was used. The absorbance in the case of the AHU1057 was regarded as a blank, and those which show a value of 0.08 or more were judged to be "reactive." The results are shown in Table 1.

Example 2

Classification Assay of the Obtained Monoclonal Antibodies

A commercially available kit (Mouse Monoclonal Antibody Isotyping Kit available from Amersham Inc.) was used to investigate the types of class and subclass, and L-chain with respect to the three antibodies obtained in Example 1. The results are shown in Table 2.

TABLE 2

| antibody | class, subclass | L-chain (type) |
| --- | --- | --- |
| BLb2F37 | IgG2b | λ |
| BG3A5b4 | IgG2b | κ |
| PQ3H8a9 | IgG2b | κ |

Example 3

Quick Identification Method and Identification Kit

The three kinds of monoclonal antibody for use that had recognized the beer spoilage lactic acid bacteria were obtained by the method as explained above.

(1) Preparation of Centrifugation Tube Equipped with a Filter (Blocking Already Done)

To a centrifugation tube with a filter (SUPREC™-01, available from Takara Shuzo Co. Ltd.) was added 100 μl of 1% casein (in PBS). After allowing to stand at room temperature for 1 h, it was centrifuged at 2000 rpm for 5 min using a centrifuge of the swing type having a radius of 16.5

TABLE 1

| | *L. brevis* | | *L. lindneri* | *P. damnosus* | | other non-beer |
| --- | --- | --- | --- | --- | --- | --- |
| antibody | beer spoilage | non-beer spoilage | beer spoilage | beer spoilage | non-beer spoilage | spoilage lactic acid bacteria |
| BLb2F37 | 44/44 | 0/18 | 0/7 | 2/3 | 0/1 | 0/47 |
| BG3A5b4 | 0/44 | 0/18 | 7/7 | 0/3 | 0/1 | 0/47 |
| PQ3H8a9 | 30/44 | 0/18 | 0/7 | 3/3 | 1/1 | 0/47 |

As is apparent from Table 1, the BLb2F37 antibody displayed reactivity against all the beer spoilage *Lactobacillus brevis* and a majority of the *Pediococcus damnosus*, but displayed no reactivity against the non-beer spoilage *Lactobacillus brevis* and other non-beer spoilage lactic acid bacteria, including the *Pediococcus damnosus*. The BG3A5b4 antibody displayed reactivity against all the beer spoilage *Lactobacillus lindneri*, but displayed no reactivity against the non-beer spoilage bacteria. The PQ3H8a9 antibody displayed reactivity against all the beer spoilage *Pediococcus damnosus* and a majority of the beer spoilage *Lactobacillus brevis*, but displayed no reactivity against the non-beer spoilage lactic acid bacteria except the one strain of non-beer spoilage *Pediococcus damnosus*.

From the findings it has been understood that the antibodies described above can be used to specifically detect beer spoilage lactic acid bacteria, namely without reacting to non-beer spoilage lactic acid bacteria. Furthermore, it has been shown that when the three kinds of antibody are combined for use, all the beer spoilage lactic acid bacteria can specifically be detected.

cm. Next, a washing solution (10 mM Tris-HCl/pH 8.0/ 0.05% TWEEN 20 (polyoxyethylene(20) sorbitan monolaurate), 200 μl, was added and centrifugation was done at 2000 rpm for 10 min. This resulted in a centrifugation tube with a filter (blocking already done), which was stored at 4° C.

(2) Antibody Solutions

Antibody BLb2F37 (for Antibody Solution I), Antibody BG3A5b4 (for Antibody Solution II), and Antibody PQ3H8a9 (for Antibody Solution III) were diluted, respectively, so as to give backgrounds at similar levels. Peroxidase-conjugated goat anti mouse IgG+IgM (H+L) (available from Wako Pure Chemicals Co. Ltd.) was diluted 50-fold. Five volume parts of the former, 5 volume parts of the latter, 7 volume parts of 1% casein (in PBS), and 33 volume parts of PBS were mixed and made small portions to be stored at −20° C. The respective solutions were denoted Antibody Solutions I–III.

Fifty microliters of each of these solutions was used per centrifugation tube with a filter.

(3) Washing Solution

Three hundred fifty microliters of 10 mM Tris-HCl (pH 8.0) containing 0.05% TWEEN 20 (polyoxyethylene(20) sorbitan monolaurate) was used per filter unit.

(4) Coloring and Quenching Solutions

A coloring kit for peroxidase (OPD) (available from Sumitomo Bakelite Co. Ltd.) was used. Fifty microliters of a color fixing agent (one tablet) dissolved in 5 ml of substrate solution was used per centrifugation tube with a filter. The same amounts of quenching solutions were used.

(5) One platinum loop of the beer spoilage bacteria preserved in NBB slants after culturing in beer or one platinum loop of the non-beer spoilage bacteria preserved in NBB slants was suspended in 100 µl of physiological saline, and 25 µl each was added to the three filter units, allowing to react with Antibody Solutions I–III, respectively. Washing and coloring were done. Consequently, in cases of the non-beer spoilage bacteria weak coloring was almost similarly observed with all the three filter units; in cases of the beer spoilage bacteria markedly stronger coloring was observed with one or two of the filter units than with the remaining filter unit(s). See FIG. 1.

The results obtained have indicated that if the present method is employed, the quantities of test bacteria need not be precise and that when the bacterium is judged to be a beer spoilage one, the identification of its kind becomes possible based on which tube (antibody) develops color.

Further, when such quick identification method was applied to all the lactic acid bacteria listed in Table 1, the results were obtained that did not contradict the antibody reactivities shown in Table 1, although not shown in the figures.

Still further, it has been clearly shown that according to the present quick identification method, adequate judgements are possible with bacterial quantities at the levels of one platinum loop.

Obviously, numerous modifications and variations of the present invention are possible in light of the above teachings. It is therefore to be understood that within the scope of the appended claims, the invention may be practiced otherwise than as specifically described herein.

This application is based on Japanese Patent Application Serial No. Hei 10-206484 filed on Jul. 22, 1998 and Japanese Patent Application Serial No. Hei 11-4096 filed on Jan. 11, 1999, which are incorporated herein by references in its entirety.

What is claimed is:

1. A hybridoma cell line, which is BLb2F37 (FERM BP-6744).

2. A hybridoma cell line, which is BG3A5b4 (FERM BP-6745).

3. A hybridoma cell line, which is PQ3H8a9 (FERM BP-6746).

4. A kit for the detection of a beer spoilage lactic acid bacterium, comprising:

(1) a centrifugation tube comprising a filter for trapping bacteria;

(2) a monoclonal antibody produced by a hybridoma cell line selected from the group consisting of BLb2F37, BG3A5b4, and PQ3H8a9;

(3) a secondary antibody against the monoclonal antibody said secondary antibody labeled with an enzyme; and (4) a substrate reacting with and coloring the enzyme used for labeling the secondary antibody.

5. A kit for the detection of a beer spoilage lactic acid bacterium, comprising:

(1) a centrifugation tube comprising a filter for trapping bacteria;

(2) a monoclonal antibody produced by a hybridoma cell line selected from the group consisting of BLb2F37, BG3A5b4, and PQ3H8a9, wherein the monoclonal antibody is labeled with an enzyme.

* * * * *